(12) United States Patent
Flohr et al.

(10) Patent No.: US 6,599,901 B1
(45) Date of Patent: Jul. 29, 2003

(54) PYRIDONE SUBSTITUTED BENZOTHIAZOLE DERIVATIVES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffman-La Roche Inc., Mutley, NJ (US)

( * ) Notice: Subject to any disclaimer, the term of this patent is extended or adjusted under 35 U.S.C. 154(b) by 0 days.

(21) Appl. No.: 10/288,531

(22) Filed: Nov. 5, 2002

(30) Foreign Application Priority Data

Nov. 19, 2001 (EP) .............................. 01127313

(51) Int. Cl.⁷ .................. A61K 31/5377; C07D 413/14
(52) U.S. Cl. ................ 514/233.8; 544/131; 544/124; 544/107; 544/106; 514/232.5; 514/237.2
(58) Field of Search .......................... 514/233.8, 237.2, 514/232.5; 544/131, 124, 107, 106

(56) References Cited

U.S. PATENT DOCUMENTS 6,521,754 B2 * 2/2003 Alainine ..................... 544/129

FOREIGN PATENT DOCUMENTS

EP 113219 7/1984

OTHER PUBLICATIONS

Poulsen et al., Bioorganic & Medicinal Chemistry, 6, pp. 619–641 (1998).
Müller et al., Bioorganic & Medicinal Chemistry, 6, pp. 707–719 (1998).
Kim et al., J. Med. Chem., 41, pp. 2835–2845 (1998).
Li et al., J. Med. Chem., 41, pp. 3186–3201 (1998).
Baraldi et al., J. Med. Chem., 41, pp. 2126–2133 (1998).
Li et al., J. Med. Chem., 42, pp. 706–721 (1999).
Baraldi et al., J. Med. Chem., 39, pp. 1164–117 (1996).
Colotta et al., Arch. Pharm. Pharm. Med. Chem., 332, pp. 39–41 (1999).
Auchampach et al., Am. J. Physiol., 276, pp. H1113–1116 (1999).
Haas et al., Naunyn Schmiedeberg's Arch. Pharmacol., 362, pp. 375–381 (2000).
Dionisotti et al., Br. J. Pharmacol., 121, pp. 353–360 (1997).
Bowman et al., Synthetic Commun., 29, pp. 4051–4059 (1999).
WO 01/97786, F. Hoffmann–La Roche AG, filed Dec. 27, 2001.

* cited by examiner

Primary Examiner—Charanjit S. Aulakh
(74) Attorney, Agent, or Firm—George W. Johnston; Patricia S. Rocha-Tramaloni; Lyman H. Smith

(57) ABSTRACT

The present invention relates to compounds of the formula

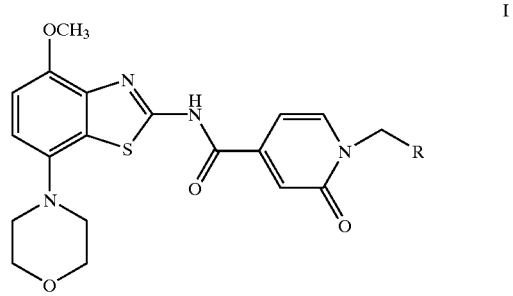

I wherein R is as defined herewithin. The compounds of formula I have a good affinity to the $A_{2A}$ receptor and therefore they may be used in the control or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, aniticonvulsants and cardioprotective agents for disorders such as coronary artery disease and heart failure.

21 Claims, No Drawings

PYRIDONE SUBSTITUTED BENZOTHIAZOLE DERIVATIVES

BACKGROUND OF THE INVENTION

The present invention generally relates to pyridone substituted benzothiazole compounds that are adenosine receptor ligands. Specifically, the compounds of the present invention have a good affinity to the $A_{2A}$-receptor and a high selectivity to the $A_1$- and $A_3$ receptors and, in addition, they have a good water solubility.

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzym A; and to RNA. Together adenosine and these related compounds are important in the regulation of many aspects of cellular metabolism and in the modulation of different central nervous system activities.

The receptores for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtyps has been classically characterised by the adenylate cyclase effector system, which utilises cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtyps is to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is a neuromodulator, able to modulate many aspects of physiological brain function. Endogenous adenosine, a central link between energy metabolism and neuronal activity, varies according to behavioulal state and (patho)physiological conditions. Under conditions of increased demand and decreased availability of energy (such as hypoxia, hypoglycemia, and/or excessive neuronal activity), adenosine provides a powerful protective fedback mechanism. Interacting with adenosine receptors represents a promising target for therapeutic intervention in a number of neurological and psychiatric diseases such as epilepsy, sleep, movement disorders (Parkinson or Huntington's disease), Alzheimer's disease, depression, schizophrenia, or addiction. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$ antagonists have therapeutic potential in the treatment of various forms of dementia, for example in Alzheimer's disease, and of neurodegenerative disorders, e.g. stroke. Adenosine $A_{2a}$ receptor antagonists modulate the activity of striatal GABAergic neurons and regulate smooth and well-coordinated movements, thus offering a potential therapy for Parkinsonian symptoms. Adenosine is also implicated in a number of physiological processes involved in sedation, hypnosis, schizophrenia, anxiety, pain, respiration, depression, and drug addiction (amphetamine, cocaine, opioids, ethanol, nicotine, cannabinoids). Drugs acting at adenosine receptors therefore have therapeutic potential as sedatives, muscle relaxants, antipsychotics, anxiolytics, analgesics, respiratory stimulants, antidepressants, and to treat drug abuse. They may also be used in the treatment of ADHD (attention deficit hyper-activity disorder).

An important role for adenosine in the cardiovascular system is as a cardioprotective agent. Levels of endogenous adenosine increase in response to ischaemia and hypoxia, and protect cardiac tissue during and after trauma (preconditioning). By acting at the $A_1$ receptor, adenosine $A_1$ agonists may protect against the injury caused by myocardial ischemia and reperfusion. The modulating influence of $A_2$a receptors on adrenergic function may have implications for a variety of disorders such as coronary artery disease and heart failure. $A_{2a}$ antagonists may be of therapeutic benefit in situations in which an enhanced antiadrenergic response is desirable, such as during acute myocardial ischemia. Selective antagonists at $A_{2a}$ receptors may also enhance the effectiveness of adenosine in terminating supraventricula arrhytmias.

Adenosine modulates many aspects of renal function, including renin release, glomerular filtration rate and renal blood flow. Compounds which antagonise the renal affects of adenosine have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201,
J. Med. Chem., (1998), 41, 2126–2133,
J. Med. Chem., (1999), 42, 706–721,
J. Med. Chem., (1996), 39, 1164–1171,
Arch. Pharm. Med. Chem., 332,339–41, (1999),
Am. J. Physiol., 276, H1113–1116, (1999) or
Naunyn Schmied, Arch. Pharmacol. 362, 375–381, (2000).

SUMMARY OF THE INVENTION

The present invention relates to compounds of the formula

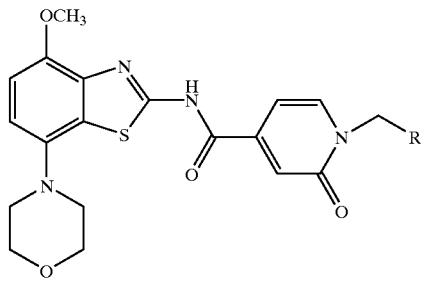

wherein R is as defined herewithin.

The present invention relates to compounds of formula I per se, the use of compounds of formula I and their pharmaceutically acceptable salts for the manufacture of medicaments for the treatment of diseases related to the adenosine $A_2$ receptor. The present invention further relates to the manufacture of compounds of formula I, medicaments based on compounds of formula I and their production, as well as the use of compounds of formula I in the control or prevention of illnesses based on the modulation of the adenosine system. These illnesses include Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents for disorders such as coronary artery disease and heart failure. The most preferred indications in accordance with the present invention are those, which base on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

The present invention relates to compounds of the formula

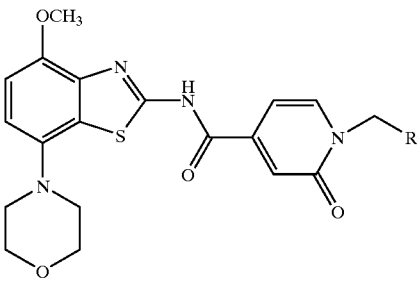

wherein

R is phenyl, pyridin-2-yl, —C(O)—O-lower alkyl, C(O)-lower alkyl, —C(O)-morpholinyl, —C(O)—NR'$_2$, —(CH$_2$)$_n$—NR'$_2$ or —(CH$_2$)$_n$—O-lower alkyl and each R' is independently hydrogen or lower alkyl;

and pharmaceutically acceptable salts thereof.

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

Preferred compounds of the present application are those, wherein R is phenyl, pyridin-2-yl, —C(O)—O—CH$_2$CH$_3$, —C(O)—CH$_2$CH$_3$, —C(O)-morpholinyl or —C(O)—N(CH$_3$)$_2$, which are the following:

1-benzyl-2-oxo-1,2-dihydro-pyridine-4-carboxylic acid (4-methoxy-7-morpholin-4-yl-benzothiazol-2-yl)-amide,

[4-(4-methoxy-7-morpholin-4-yl-benzothiazol-2-yl-carbamoyl)-2-oxo-2H-pyridin-1-yl]-acetic acid ethyl ester, 2-oxo-1-(2-oxo-butyl)-1,2-dihydro-pyridine-4-carboxylic acid (4-methoxy-7-morpholin-4-yl-benzothiazol-2-yl)-amide, 2-oxo-1-pyridin-2-yl-methyl-1,2-dihydio-pyridine-4-carboxylic acid (4-methoxy-7-morpholin-4-yl-benzothiazol-2-yl)-amide, 1-(2-morpholin-4-yl-2-oxo-ethyl)-2-oxo-1,2-dihydro-pyridine-4-carboxylic acid (4-methoxy-7-morpholin-4-yl-benzothiazol-2-yl)-amide or 1-dimethylcarbamoylmethyl-2-oxo-1,2-dihydro-pyridine-4-carboxylic acid (4-methoxy-7-morpholin-4-yl-benzothiazol-2-yl)-amide.

The present compounds of formula I and their pharmaceutically acceptable salts can be prepared by methods known in the art, for example, by processes described below, which processes comprise a) reacting a compound of formula (6)

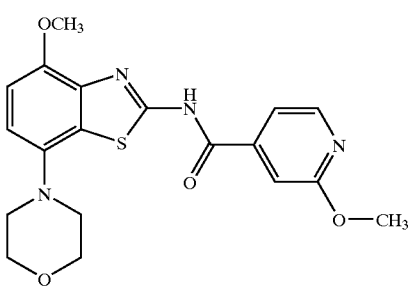

with a compound of formula (7)

to yield a compound of formula I

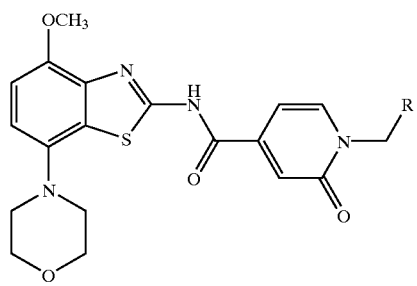

wherein R is phenyl, pyridyl, —C(O)O-lower alkyl or —C(O)-lower alkyl, or b) reacting, a compound of formula (8)

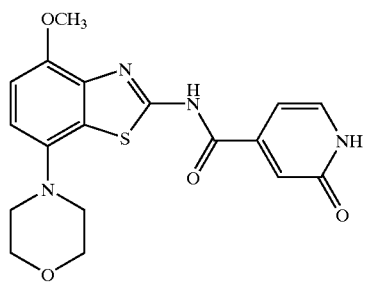

with a compound of formula (7)

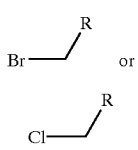

or (9)

to yield a compound of formula I

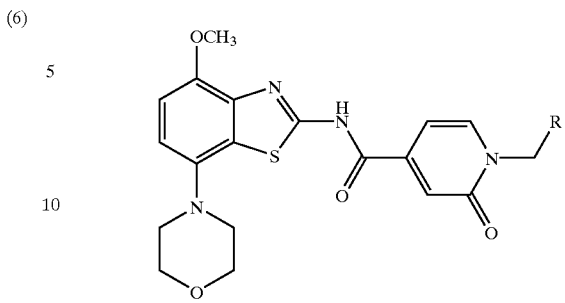

wherein R is —C(O)-morpholinyl, —(CH$_2$)$_n$—O-lower alkyl, —(CH$_2$)$_n$NR'$_2$ or —C(O)NR'$_2$, and if desired, converting the compounds obtained into pharmaceutically acceptable acid addition salts.

Preparation of Compounds of Formula I Wherein R is Phenyl, Pyridyl, —C(O)O-Lower Alkyl or C(O)-Lower Alkyl One method of preparation of compounds of formula I, wherein R is phenyl, pyridyl, —C(O)O-lower alkyl or C(O)-lower alkyl, is from a 2-methoxy-isonicotinamide intermediate of formula (6), as shown in reaction Schemes 1 and 2 below.

Scheme 1

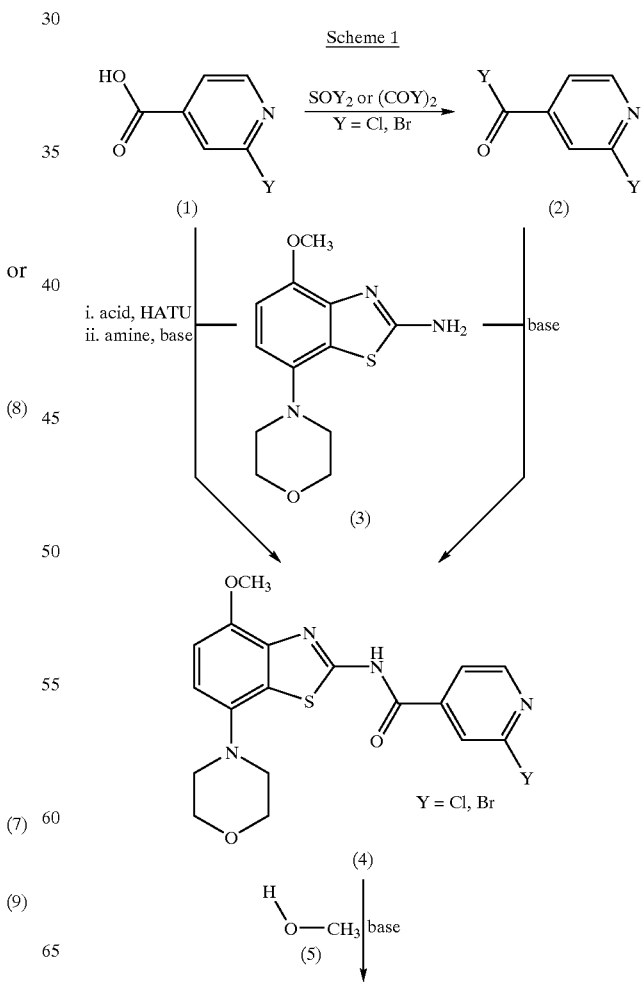

-continued

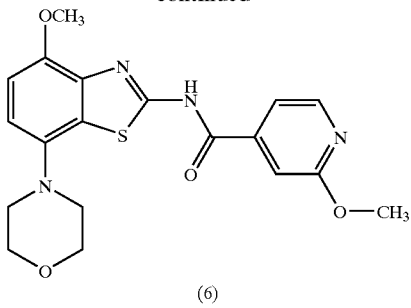

(6)

In this scheme the following abbreviation has been used: HATU O-(7-azabenzotriazol-1-yl)-N,N,N',N'-tetramethyluronium hexafluorophosphate Scheme 2

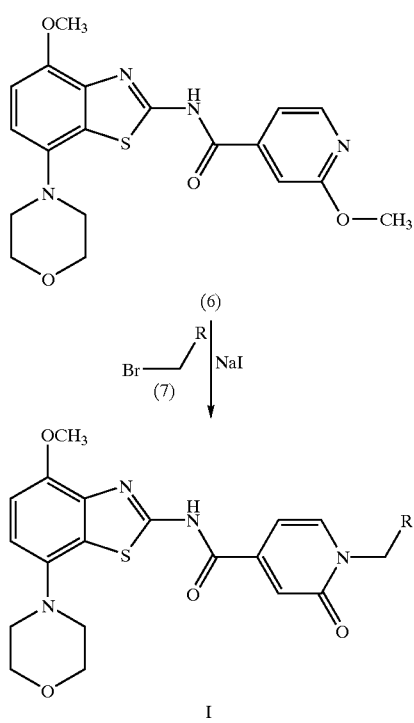

wherein R is phenyl, pyridyl, —C(O)O-lower alkyl or C(O)-lower alkyl.

Preparation of Compounds of Formula (2)

The starting 2-chloroisonicotinic acid or 2-bromoisonicotinic acid of formula (1) may be obtained commercially, for example from Maybridge Chemicals, or may be prepared according to methods well known in the art.

The 2-haloisonicotinic acid of formula (1) may be converted to the corresponding acyl halide derivative of formula (2) by reacting a compound of formula (1) with an excess of a halogenating agent, such as oxalyl chloride or oxalyl bromide, or thionyl chloride or thionyl bromide, using a catalyst such as N,N-dimethylformamide or pyridine, in an organic solvent, prefereably dichloromethane or dichloroethane, at room temperature for about 2–16 hours, preferably 16 hours. The product of formula (2) is isolated by conventional means, and preferably reacted in the next step without further purification.

Preparation of Compounds of Formula (4)

The starting 2-amino-benzothiazole compound of formula (3) may be prepared according to methods disclosed in EP 00113219.0.

The compounds of formula (4) are prepared by treating the 2-amino-benzothiazole compounds of formula (3) with a slight excess of the acyl halide compounds of formula (2) in a non-protic organic solvent, preferably a mixture of dichloromethane and tetrahydrofuran, containing a base, preferably N-ethyldiisopropylamine or triethylamine, at room temperature for 2–24 hours, preferably 24 hours. The product of formula (4) is isolated by conventional means, and preferably purified by means of chromatography or recrystallization.

Alternative Preparation of Compounds of Formula (4)

The compounds of formula (4) may also be prepared directly from compounds of formula (1). In this method, the compound of formula (1) is treated with a stoichiometric equivalent of a peptide-coupling reagent, preferably O-(7-azabenzotriazol-1-yl)-N,N,N',N'-tetramethyluronium hexatluorophosphate (HATU), in an ethereal solvent, preferably tetrahydrofuran, containing a base, preferably N-ethyldiisopropylamine, at room temperature for 30–90 minutes. This mixture is then treated with a 2-amino-benzothiazole compound of formula (3) in a solvent mixture, preferably a mixture of tetrahydrofuran, dioxane and N,N-dimethylformamide, at room temperature for 16–24 hours, preferably 24 hours. The product of formula (4) is isolated by conventional means, and preferably purified by means of chromatography or recrystallization.

Preparation of Compounds of Formula (6)

One method of preparation of a compound of formula (6) is by treatment of a compound of formula (4) with an excess of methanol, together with a metal-hydride base, preferably sodium hydride or potassium hydride. These reactions may be carried out in an ethereal solvent such as such as dioxane, tetrahydrofuran or 1,2-dimethoxyethane, preferably dioxane, optionally containing a co-solvent such as N,N-dimethylformamide, at a temperature between room temperature and the reflux temperature of the solvent, preferably about 100° C., for 2–72 hours, preferably 16 hours. The product of formula (6) is isolated by conventional means, and preferably purified by means of chromatography or recrystallization.

The compound of formula (6) is treated with an excess of an alkyl bromide of formula (7), which may be commercially available or may be prepared by methods well known in the art, according to the procedure of Synthetic Commun. 1999, 29, 4051–4059. These reactions may be carried out in a polar organic solvent such as acetonitrile or N,N-dimethylformamide, preferably N,N-dimethylformamide, at an elevated temperature, preferably the reflux temperature of the solvent used, for 2–18 hours, preferably 16 hours. The product of formula I, where R is phenyl, pyridyl, —C(O)O-lower alkyl or C(O)-lower alkyl, is isolated by conventional means, and preferably purified by means of chromatography or recrystallization.

Preparation of Compounds of Formula I, Wherein R is —C(O)-Morpholinyl, —(CH$_2$)$_n$—NR'$_2$, —(CH$_2$)$_n$—O-Lower Alkyl or C(O)NR'$_2$ One method of preparation of compounds of formula I, wherein R is —C(O)-morpholinyl, —(CH$_2$)$_n$—NR'$_2$, —(CH$_2$)$_n$—O-lower alkyl or C(O)NR'$_2$, is from a 2-oxo-1,2-dihydro-pyridine-4-carboxylic acid amide intermediate of formula (8), the preparation of which is shown in reaction scheme 3 below.

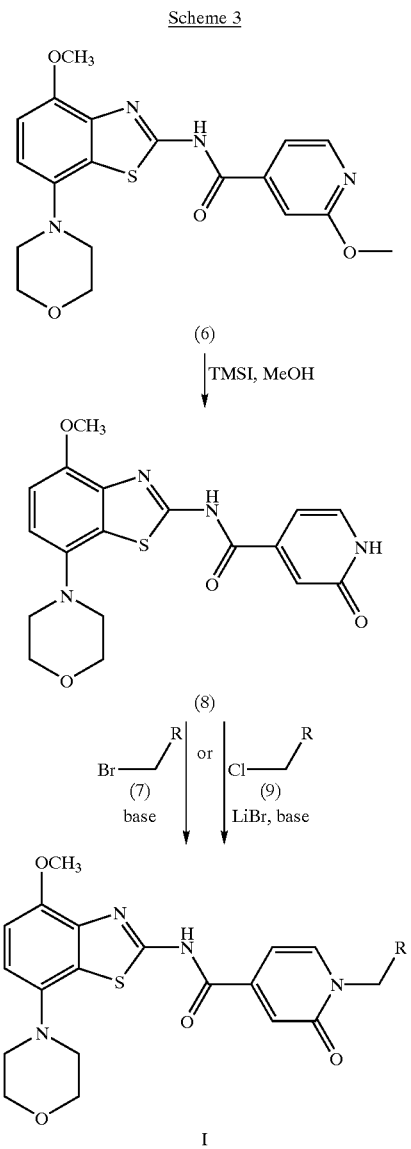

Scheme 3 wherein R is —C(O)-morpholinyl, —(CH$_2$)$_n$—NR'$_2$, —(CH$_2$)$_n$—O-lower alkyl, or —C(O)NR'$_2$ and TMSI is iodotrimethylsilane.

Preparation of Compounds of Formula (8)

The compound of formula (6) is treated with an excess of iodotrimethylsilane in a halogenated organic solvent, preferably chloroform, at room temperature or above, preferably at the reflux temperature of the solvent, for 2–16 hours, preferably about 8 hours. The reaction mixture is then treated with an alcohol, preferably methanol, at room temperature or above, preferably at the reflux temperature of the solvent mixture, for 2–18 hours, preferably about 16 hours. The product of formula (8) is isolated by conventional means, and preferably purified by means of chromatography or recrystallization.

Preparation of Compounds of Formula I, Wherein R is —C(O)-Morpholinyl, —(CH$_2$)$_n$—NR'$_2$, —(CH$_2$)$_n$—O-Lower Alkyl or —C(O)NR'$_2$ The compound of formula (8) is treated with an excess of an alkyl bromide of formula (7) or an alkyl chloride of formula (9), which may be commercially available or maybe prepared by methods well known in the art. In the case where an alkyl chloride of formula (9) is used, the reaction is performed in the presence of a stoichiometric equivalent of lithium bromide. These reactions may be carried out in a polar organic solvent such as dioxane or N,N-dimethylformamide, preferably a mixture of N,N-dimethylformamide and dioxane, at a temperature between room temperature and the reflux temperature of the solvent mixture used, for 2–18 hours, preferably 16 hours. The product of formula I is isolated by conventional means, and preferably purified by means of chromatography or recrystallization.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it could be demonstrated that the compounds of the present invention are adenosine receptor ligands and possess a high affinity towards the adenosine A$_{2A}$ receptor and a good selectivity towards A$_1$ receptor.

The compounds were investigated in accordance with the tests given hereinafter.

Human Adenosine A$_1$ Receptor

The human adenosine A$_1$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM CaCl$_2$ and 10 mM MgCl$_2$ (pH 7.4) (buffer A). The [$^3$H]-DPCPX (([propyl-$^3$H]8-cyclopentyl-1,3-dipropyxanthine); 0.6 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. IC$_{50}$ values were calculated using a non-linear curve fitting program and Ki values calculated using the Cheng-Prussoff equation.

Human Adenosine A$_{2A}$ Receptor

The human adenosine A$_{2A}$ receptor was recombinantly expressed in chinese hamster ovary (CHO) cells using the semliki forest virus expression system. Cells were harvested, washed twice by centrifugation, homogenised and again washed by centrifugation. The final washed membrane pellet was suspended in a Tris (50 mM) buffer containing 120 mM NaCl, 5 mM KCl, 2 mM CaCl$_2$ and 10 mM MgCl$_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µM of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. IC$_{50}$ values were calculated using a non-linear curve fitting program and Ki values calculated using the Cheng-Prussoff equation.

It has been shown that compounds of formula I have a good affinity to the A$_{2A}$ receptor and a high selectivity toward the A$_1$ receptor. The preferred compounds show a pKi>7.2, as described in the table below:

| Example No. | hA$_1$ (pKi) | hA$_2$ (pKi) |
|---|---|---|
| 1 | 5.90 | 8.67 |
| 2 | 5.18 | 8.19 |
| 3 | 5.18 | 8.24 |
| 4 | 5.18 | 8.10 |
| 5 | 5.18 | 7.23 |
| 6 | 5.18 | 7.30 |

The compounds of formula I and the pharmaceutically acceptable salts of the compounds of formula I can be used as medicaments, e.g. in the form of pharmaceutical preparations. The pharmaceutical preparations can be administered orally, e.g. in the form of tablets, coated tablets, dragees, hard and soft gelatine capsules, solutions, emulsions or suspensions. The administration can, however, also be effected rectally, e.g. in the form of suppositories, parenterally, e.g. in the form of injection solutions.

The compounds of formula I can he processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active. Substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or anti-oxidants. They can also contain still other therapeutically valuable substances.

Medicaments containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Tablet Formulation (Wet Granulation)

| Item | Ingredients | mg/tablet | | | |
|---|---|---|---|---|---|
| | | 5 mg | 25 mg | 100 mg | 500 mg |
| 1. | Compound of formula I | 5 | 25 | 100 | 500 |
| 2 | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| Item | Ingredient | mg/capsule | | | |
|---|---|---|---|---|---|
| | | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

1-Benzyl-2-oxo-1,2-dihydro-pyridine-4-carboxylic Acid (4-Methoxy-7-morpholin-4-yl-benzothiazol-2-yl)-amide To a stirred solution of 85 mg (0.21 mmol) 2-methoxy-N-(4-methoxy-7-morpholin-4-yl-benzothiazol-2-yl)-isonicotinamide in 2 ml acetonitrile were added 73 mg (0.43 mmol) sodium iodide and 0.05 ml (0.43 mmol) benzyl bromide. The mixture was heated at reflux for 16 h. The reaction mixture was then cooled to room temperature, diluted with ethyl acetate, and washed sequentially with water and saturated brine. The organic phase was then dried over sodium sulfate and concentrated in vacuo. Flash chromatography (2/1 EtOAc/toluene) afforded 32 mg (32%) 1-benzyl-2-oxo-1,2-dihydro-pyridine-4-carboxylic acid (4-methoxy-7-morpholin-4-yl-benzothiazol-2-yl)-amide as a yellow crystalline solid. ES-MS m/e (%)): 499 (M+Na$^+$, 14), 477 (M+H$^+$, 100).

In an analogous manner there were obtained:

EXAMPLE 2

[4-(4-Methoxy-7-morpholin-4-yl-benzothiazol-2-ylcarbamoyl)-2-oxo-2H-pyridin-1-yl]-acetic Acid Ethyl Ester From 2-methoxy-N-(4-methoxy-7-morpholin-4-yl-benzothiazol-2-yl)-isonicotinamide with sodium iodide and ethyl bromoacetate in DMF. ES-MS m/e (%): 495 (M+Na$^+$, 25), 473 (M+H$^+$, 100).

EXAMPLE 3

2-oxo-1-(2-oxo-Butyl)-1,2-dihydro-pyridine-4-carboxylic Acid (4-Methoxy-7-morpholin-4-yl-benzothiazol-2-yl)-amide From 2-methoxy-N-(4-methoxy-7-morpholin-4-yl-beinzothiazol-2-yl)-isonicotinamide with sodium iodide and 1-bromo-2-butanone in DMF. ES-MS m/e (%): 479 (M+Na$^+$, 32), 457 (M+H$^+$, 100).

EXAMPLE 4

2-oxo-1-Pyridin-2-ylmethyl-1,2-dihydro-pyridine-4-carboxylic Acid (4-Methoxy-7-morpholin-4-yl-benzothiazol-2-yl)-amide From 2-methoxy-N-(4-methoxy-7-morpholin-4-yl-benzothiazol-2-yl)-isonicotinamide with sodium iodide and 2-(bromoethyl)pyridine hydrobromide in DMF. ES-MS m/e (%): 500 (M+Na$^+$, 30), 478 (M+H$^+$, 100).

EXAMPLE 5

1-(2-Morpholin-4-yl-2-oxo-ethyl)-2-oxo-1,2-dihydro-pyridine-4-carboxylic Acid (4-Methoxy-7-morpholin-4-yl-benzothiazol-2-yl)-amide To a stirred solution of 200 mg (0.52 mmol) 2-oxo-1,2-dihydro-pyridine-4-carboxylic acid (4-methoxy-7-morpholin-4-yl-benzothiazol-2-yl)-amide in 1 ml DMF and 4 ml 1,2-dimethoxyethane was added 44 mg (1.04 mmol) sodium hydride (60% dispersion in mineral oil). After stirring for 15 min at room temperature, 90 mg (1.04 mmol) lithium bromide was added and stirring continued for a further 15 min. 95 mg (0.58 mmol) 4-(2-chloroacetyl) morpholine was then added and the mixture was stirred at room temperature for 16 h. The reaction mixture was then diluted with ethyl acetate, and washed sequentially with 0.5 M hydrochloric acid, saturated sodium bicarbonate solution and saturated brine. The combined aqueous phases were filtered, and the filter cake washed with ether, then resuspended in toluene and concentrated in vacuo. Flash chromatography (MeOH/CH2Cl2) followed by trituration in ethyl acetate afforded 83 mg (31%) 1-(2-morpholin-4-yl-2-oxo-ethyl)-2-oxo-1,2-dihydro-pyridine-4-carboxylic acid (4-methoxy-7-morpholin-4-yl-benzothiazol-2-yl)-amide as a yellow crystalline solid. ES-MS m/e (%): 536 (M+Na$^+$, 25), 514 (M+H$^+$, 100).

In an analogous manner there were obtained:

EXAMPLE 6

1-Dimethylcarbamoylmethyl-2-oxo-1,2-dihydro-pyridine-4-carboxylic Acid (4-Methoxy-7-morpholin-4-yl-benzothiazol-2-yl)-amide From 2-oxo-1,2-dihydro-pyridine-4-carboxylic acid (4-methoxy-7-morpholin-4-yl-benzothiazol-2-yl)-amide with sodium hydride, lithium bromide and 2-chloro-N,N-thylacetamide in 1,2-dimethoxyethane and DMF. ES-MS m/e (%): 494 (M+Na$^+$, 22), (M+H$^+$, 100).

We claim:

1. A compound of the formula I

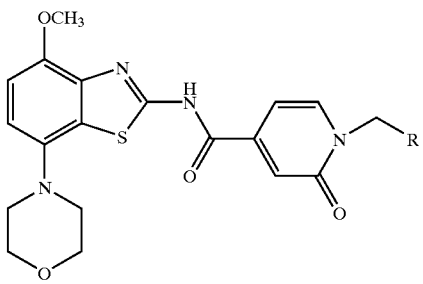

wherein

R is phenyl, pyridin-2-yl, —C(O)—O-lower alkyl, C(O)-lower alkyl, —C(O)-morpholinyl, —C(O)—NR'$_2$, —(CH$_2$)$_n$—NR'$_2$ or —(CH$_2$)$_n$—O-lower alkyl and each R' is independently hydrogen or lower alkyl;

and pharmaceutically acceptable salts thereof.

2. The compound according to claim 1, wherein R is phenyl.

3. The compound according to claim 2, wherein the compound is 1-benzyl-2-oxo-1,2-dihydro-pyridine-4-carboxylic acid (4-methoxy-7-morpholin-4-yl-benzothiazol-2-yl)-amide.

4. The compound according to claim 1, wherein R is —C(O)O-lower alkyl.

5. The compound according to claim 4, wherein the compound is [4-(4-methoxy-7-morpholin-4-yl-benzothiazol-2-ylcarbamoyl)-2-oxo-2H-pyridin-1-yl]-acetic acid ethyl ester.

6. The compound according to claim 1, wherein R is —C(O)-lower alkyl.

7. The compound according to claim 6, wherein the compound is 2-oxo-1-(2-oxo-butyl)-1,2-dihydro-pyridine-4-carboxylic acid (4-methoxy-7-morpholin-4-yl-benzothiazol-2-yl)-amide.

8. The compound according to claim 1, wherein R is pyridinyl.

9. The compound according to claim 8, wherein the compound is 2-oxo-1-pyridin-2-yl-methyl-1,2-dihydro-pyridine-4-carboxylic acid (4-methoxy-7-morpholin-4-yl-benzothiazol-2-yl)-amide.

10. The compound according to claim 1 wherein R is —C(O)-morpholinyl.

11. The compound according to claim 10, wherein the compound is 1-(2-morpholin-4-yl-2-oxo-ethyl)-2-oxo-1,2-dihydro-pyridine-4-carboxylic acid (4-methoxy-7-morpholin-4-yl-benzothiazol-2-yl)-amide.

12. The compound according to claim 1, wherein R is —C(O)-NR'$_2$.

13. The compound according to claim 12, wherein the compound is 1-dimethylcarbamoylmethyl-2-oxo-1,2-dihydro-pyridine-4-carboxylic acid (4-methoxy-7-morpholin-4-yl-benzothiazol-2-yl)-amide.

14. A process for preparing a compound of formula I as defined in claim 1, which process comprises reacting a compound of formula

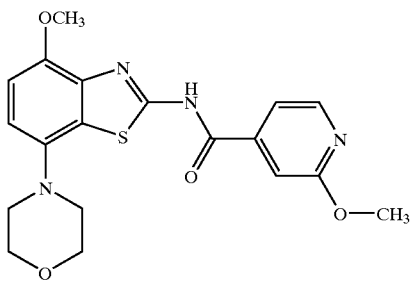

(6)

with a compound of formula

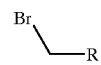

(7)

to yield a compound of formula

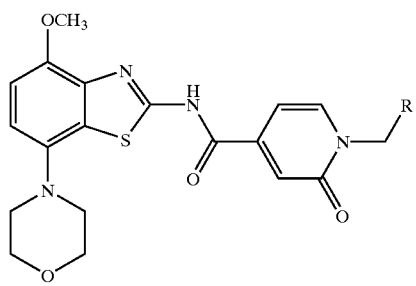

I wherein R is phenyl, pyridyl, —C(O)O-lower alkyl or —C(O)-lower alkyl.

15. A process for preparing a compound of formula I as defined in claim 1, which process comprises reacting a compound of formula

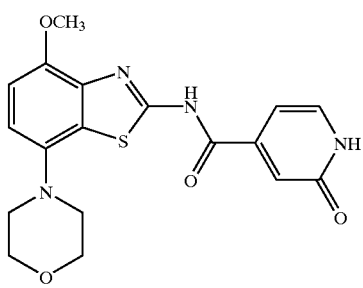

(8)

with a compound of formula

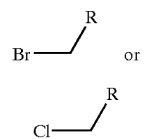

(7)

or (9)

to yield a compound of formula

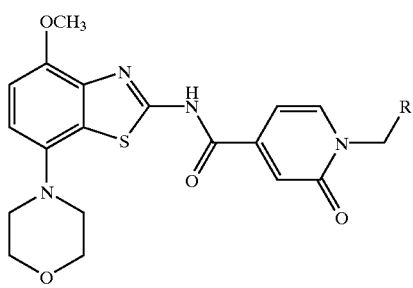

wherein R is —C(O)-morpholinyl, —(CH$_2$)$_n$—O-lower alkyl, —(CH$_2$)$_n$NR'$_2$ or —C(O)NR'$_2$.

16. The process according to claim 15, further comprising converting the compounds obtained into pharmaceutically acceptable acid addition salts.

17. A method of treating a disease mediated by the adenosine A$_1$ or A$_{2A}$ receptor comprising administering to a patient in need of such treatment, an effective amount of a compound of the formula I

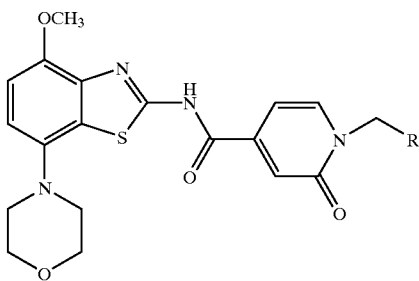

wherein
R is phenyl, pyridin-2-yl, —C(O)—O-lower alkyl, C(O)-lower alkyl, —C(O)-morpholinyl, —C(O)—NR'$_2$, —(CH$_2$)$_n$—NR'$_2$ or —(CH$_2$)$_n$—O-lower alkyl and each R' is independently hydrogen or lower alkyl;

and pharmaceutically acceptable salts thereof.

18. The method according to claim 17, wherein said disease is selected from at least one of Alzheimer's disease, Parkinson's disease, Huntington's disease, neuroprotection, schizophrenia, anxiety, pain, respiration deficits, depression, drug addiction, asthma, allergic responses, hypoxia, ischaemia, seizure, and attention deficit hyperactivity disorder.

19. The method according to claim 17, wherein said adenosine receptor is the A$_{2A}$ receptor.

20. The method according to claim 19, wherein said disease is selected from the group consisting of Alzheimer's disease, depression, drug addiction, neuroprotection, Parkinson's disease, and attention deficit hyperactivity disorder.

21. A pharmaceutical composition comprising a pharmaceutically effective amount of a compound of the formula I

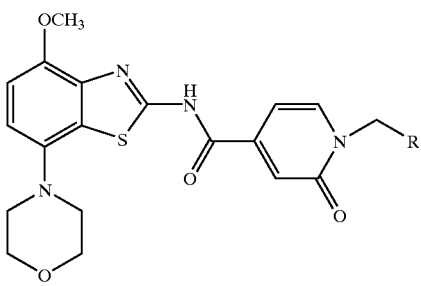

wherein
R is phenyl, pyridin-2-yl, —C(O)—O-lower alkyl, C(O)-lower alkyl, —C(O)-morpholinyl, —C(O)—NR'$_2$, —(CH$_2$)$_n$—NR'$_2$ or —(CH$_2$)$_n$—O-lower alkyl and each R' is independently hydrogen or lower alkyl;
and pharmaceutically acceptable salts thereof; and
a pharmaceutically acceptable carrier.

* * * * *

UNITED STATES PATENT AND TRADEMARK OFFICE
CERTIFICATE OF CORRECTION

PATENT NO.     : 6,599,901 B1
DATED          : July 29, 2003
INVENTOR(S)    : Alexander Flohr et al.

It is certified that error appears in the above-identified patent and that said Letters Patent is hereby corrected as shown below:

<u>Title page,</u>
Item [73], Assignee, delete "Hoffman-La Roche Inc., Mutley, NJ (US)" and insert -- Hoffmann-La Roche Inc., Nutley, NJ (US) --.

Signed and Sealed this

Eighteenth Day of November, 2003

JAMES E. ROGAN
*Director of the United States Patent and Trademark Office*